(12) United States Patent
Porter et al.

(10) Patent No.: US 6,523,392 B2
(45) Date of Patent: Feb. 25, 2003

(54) MICROCANTILEVER SENSOR

(75) Inventors: Timothy L. Porter, Flagstaff, AZ (US); Michael P. Eastman, Flagstaff, AZ (US)

(73) Assignee: Arizona Board of Regents, Tempe, AZ (US)

(*) Notice: Subject to any disclaimer, the term of this patent is extended or adjusted under 35 U.S.C. 154(b) by 0 days.

(21) Appl. No.: 09/768,647

(22) Filed: Jan. 24, 2001

(65) Prior Publication Data
US 2003/0010097 A1 Jan. 16, 2003

Related U.S. Application Data
(60) Provisional application No. 60/178,530, filed on Jan. 25, 2000.

(51) Int. Cl.[7] .................. G01N 27/00; G01N 19/00; C12Q 1/00; C12Q 1/08
(52) U.S. Cl. .............. 73/24.01; 73/24.06; 73/31.05; 73/592; 73/580; 422/88
(58) Field of Search ................ 73/24.01, 24.06, 73/61.72, 31.05, 580, 592; 422/88

(56) References Cited

U.S. PATENT DOCUMENTS

| | | | | |
|---|---|---|---|---|
| 3,260,104 A | * | 7/1966 | King, Jr. ............... | 73/23 |
| 4,361,026 A | * | 11/1982 | Muller et al. .......... | 73/23 |
| 5,028,394 A | * | 7/1991 | Lowell, Jr. et al. ..... | 422/58 |
| 5,445,008 A | * | 8/1995 | Wachter et al. ........ | 73/24.06 |
| 5,536,963 A | * | 7/1996 | Polla .................. | 257/417 |
| 5,679,888 A | * | 10/1997 | Tohda et al. .......... | 73/105 |
| 5,719,324 A | * | 2/1998 | Thjundat et al. ....... | 73/24.01 |
| 5,877,411 A | * | 3/1999 | Namerikawa et al. .... | 73/64.53 |
| 5,955,659 A | * | 9/1999 | Gupta et al. .......... | 73/54.01 |
| 6,016,686 A | * | 1/2000 | Thundat ............... | 73/23.2 |
| 6,041,642 A | * | 3/2000 | Duncan ................ | 73/24.01 |
| 6,109,852 A | * | 8/2000 | Shahinpoor et al. ..... | 414/1 |
| 6,183,097 B1 | * | 2/2001 | Saif et al. ........... | 359/871 |
| 6,196,052 B1 | * | 3/2001 | May et al. ............ | 73/24.06 |
| 6,201,980 B1 | * | 3/2001 | Darrow et al. ......... | 600/347 |
| 6,287,765 B1 | * | 9/2001 | Cubicciotti ........... | 435/6 |
| 6,289,717 B1 | * | 9/2001 | Thundat et al. ........ | 73/23.2 |
| 6,303,288 B1 | * | 10/2001 | Furcht et al. ......... | 435/4 |
| 6,447,887 B1 | * | 9/2002 | Claus et al. .......... | 428/209 |

OTHER PUBLICATIONS

Eastman et al., "Application of the Solubility Parameter Concept to the Design of Chemiresistor Arrays," Journal of the Electrochemcial Society, 1999, 146, pp. 3907–3913.

Fritz et al., "Translating Biomolecular Recognition into Nanomechanics," Science, vol. 288, Apr. 14, 2000, pp. 316–318.

(List continued on next page.)

Primary Examiner—Hezron Williams
Assistant Examiner—David J. Wiggins
(74) Attorney, Agent, or Firm—Christie, Parker & Hale, LLP

(57) ABSTRACT

An apparatus and method for sensing chemical and/or biological analytes includes a deflectable arm of a microcantilever formed over and contacting a sensing element. A gaseous or liquid medium which may include the analyte being detected, is introduced to the sensing element. The sensing element undergoes volumetric expansion or contraction in the presence of the analyte sought to be detected, typically by adsorbing the analyte. The volumetric change of the sensing element causes the deflectable arm to deflect. The deflectable arm includes at least one measurable physical property which changes when the arm deflects. Detecting means are provided to measure the change in the physical property to determine the presence and amount of analyte present. An array of microcantilevers in which each microcantilever is dedicated to detecting a particular analyte which may be included in the medium, is also provided.

34 Claims, 3 Drawing Sheets

OTHER PUBLICATIONS

Lonergan et al., "Array–Based Vapor Sensing Using Chemically Sensitive, Carbon Black–Polymer Resistors," American Chemical Society (Chem Mater), 1996, 8, pp. 2298–2312.

Ricco et al., "Chemically Sensitive Interfaces on Surface Acoustic Wave Devices," Interfacial Design and Chemical Sensing, Washington, D.C., 1994, pp. 264–279.

Wachter et al., "Microchemical sensors for chemical and physical measurements," Rev. Sci. instrum., 66 (6), Jun. 1995, pp. 3662–3667.

* cited by examiner

MICROCANTILEVER SENSOR

CROSS-REFERENCE TO RELATED APPLICATIONS

This application claims priority of U.S. Provisional Application Serial No. 60/178,530, inventors Timothy L. Porter and Michael P. Eastman, entitled MICRO-CANTILEVER SENSOR filed on Jan. 25, 2000.

STATEMENT REGARDING FEDERALLY SPONSORED RESEARCH OR DEVELOPMENT

Financial assistance for this project was provided by U.S. Government Grant Number DMR-9703840; and the United States Government may own certain rights to this invention.

FIELD OF THE INVENTION

The present invention relates most generally to microsensors for sensing chemical or biological analytes. More particularly, the present invention is related to deflectable microcantilever sensors used to sense the presence of chemical and/or biological analytes

BACKGROUND OF THE INVENTION

The construction of rugged, cheap, reliable and small chemical microsensors whose output can be expressed in terms of a measurable electrical signal such as DC conductivity is of current interest. It is desired to construct devices that can detect and identify chemical or biological analytes alone or in a complex mixture. Ideally, such sensors should be able to function in either a liquid or vapor environment. Among the systems receiving attention in this regard are carbon-black organic polymer composites which are deposited by spin or drop coating on interdigitated arrays. Inclusion of the carbon-black component into the active sensor material is for the sole purpose of obtaining a measurable DC conductivity through the non-conductive active polymer material. The introduction of analyte material causes polymer swelling and consequent resistance changes of the polymer films. To identify specific vapors from a suite of possible substances and to determine the concentration of that vapor or to carry out similar measurements on multi-component systems requires the construction of arrays of sensing elements. Pattern recognition techniques or principal component analysis of the output of an array of sensors can be used for purposes of analyte identification and quantification.

A number of shortcomings are associated with the use of the carbon-black organic polymer composites. First, it is difficult to reliably reproduce the performance characteristics of a given set of chemiresistor elements due to uncontrollable variations in composite construction. Second, spin coated or drop coated carbon-black polymer composites are inherently metastable in nature and may change or degrade with time. Third, metastable composite systems may not reliably adhere to a substrate surface. Fourth, repeated exposure of the metastable sensor element to analyte vapor may lead to misleading drifts and/or changes in performance characteristics. Fifth, the carbon in a composite material may slowly release analyte material following exposure to analyte and thus have a slow recovery time. Sixth, the interdigitated arrays generally consist of two components—a glass substrate and a metallic thin film or wire along with interface regions. Such complicated structures can lead to adhesion problems. Furthermore, carbon-black cannot be used for biological sensing because sensors based on biological molecules and attached to a substrate cannot effectively incorporate a material such as carbon-black.

Another approach for sensing analytes includes the use of vibrating microcantilever structures. Using this technique, a microcantilever is driven into oscillation at one of its resonant frequencies using external circuitry. The microcantilever itself is coated with an active sensing material. Absorption of analyte molecules on the vibrating cantilever changes the frequency or amplitude of the oscillation and this change is sensed by the electronic circuitry. There are, however, several shortcomings associated with the use of vibrating or oscillating microcantilevers. The sensing materials coated on the microcantilevers can easily delaminate during use. Sensors based on this technology require extensive electronic circuitry, both to drive the microcantilevers into oscillation and to sense the change in microcantilever frequency and/or amplitude upon exposure to analyte. Additionally, fabricating arrays consisting of many, close packed vibrating cantilevers is extremely difficult due to differences in cantilever resonant frequencies and the proximity of the cantilevers to one another. Finally, these vibrating or oscillating microcantilever sensing devices are highly subject to external vibration or movement, making fabrication of truly portable devices difficult. The present invention addresses the shortcomings of each of the foregoing microsensor technologies and provides a microsensor which uses a microcantilever and a sensing element formed beneath the microcantilever and in contact with the microcantilever. The sensing material is chosen so that in the presence of the desired analyte material, the sensing element undergoes a volumetric expansion or contraction including in the vertical direction. Such a volumetric change causes the upward or downward deflection of the initially stationary microcantilever. The microcantilever includes at least one measurable physical property which changes when the microcantilever deflects in response to the volumetric change of the subjacent sensing material. The microcantilever need not be driven onto oscillation so the associated extensive electronic circuitry is not required.

SUMMARY

The present invention provides a method and apparatus for determining the presence and quantity of biological and/or chemical analytes. A deflectable arm of a microcantilever is disposed over and in contact with a sensing material formed on a surface. The sensing material is chosen to undergo a volumetric expansion or contraction in response to the presence of an analyte or analytes desired to be detected. A volumetric change in a vertical direction of the sensing material causes the deflectable arm of the microcantilever to deflect. The deflecting arm includes at least one measurable physical property which changes when the deflectable arm deflects. This change is measured to determine the presence and quantity of the analyte or analytes of interest.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

The present invention provides a method and apparatus for detecting the presence and quantity of an analyte in a gaseous or liquid medium by introducing the medium to a sensing material formed on a surface. Located superjacent and in contact with the sensing element is a deflectable arm of a microcantilever. In the presence of the analyte sought to be detected, the sensing material undergoes a volumetric expansion including in the vertical direction. Such expansion causes the deflectable arm to deflect upward. According to an alternative embodiment, in the presence of the targeted analyte, the sensing material may undergo volumetric contraction in the vertical direction which causes the downward displacement of the deflectable arm of the microcantilever. The sensing material may be a chemical sensor material such as a polymer or a biological sensor material such as a biomolecule. The sensing material may be formed in a discrete portion to be aligned beneath the deflectable arm or a continuous coating of the sensing element may be formed over the surface.

The microcantilever is formed on a substrate separate from the surface including the sensing material. Conventional semiconductor processing technology may be used to form the microcantilever. Various configurations and orientations of the microcantilever may be used. The microcantilever includes an overhang portion which extends over the edge of the microcantilever substrate and allows for the substrate and the surface containing the sensing material to be positioned in close proximity to one another such that the deflectable arm of the microcantilever is situated above and in contact with the sensing material. A micromanipulator may be used to position and align the components. The deflectable arm of the microcantilever includes at least one measurable physical property which changes when the deflectable arm deflects responsive to a volumetric change of the subjacent contiguous sensing material. The present invention also provides detecting means such as various electric circuits which detect the change in the measurable physical property or properties of the deflectable arm. The measurable physical property will preferably be measured prior to and after the introduction of the medium which may include the analyte sought to be detected. The medium is introduced to intimately contact the sensing material. The deflectable arm will preferably be formed of semiconductor materials resistant to attack by analytes and the gaseous and liquid media which are introduced to the arrangement and which may include the targeted analyte. The deflectable arm is usable in both gaseous and liquid environments.

Figure 1:
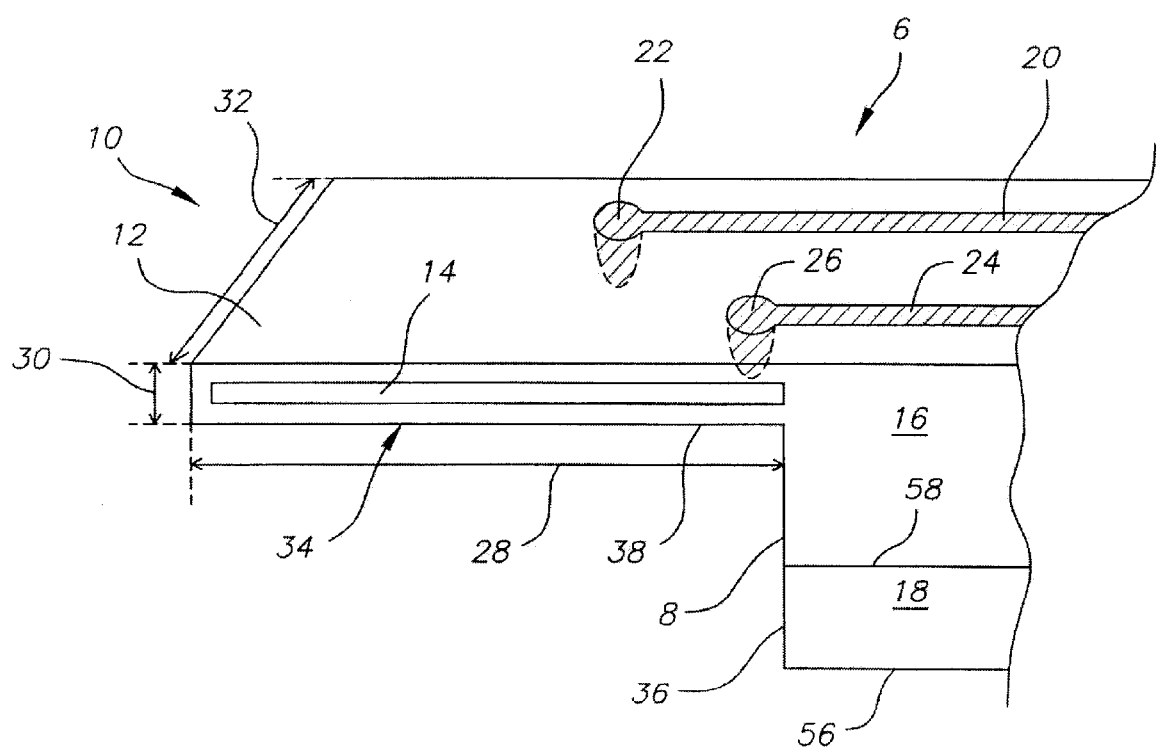
FIG. 1 is a cross-sectional, perspective view of an exemplary embodiment of a microcantilever sensor according to the present invention.

Now turning to the figures, FIG. 1 shows an exemplary embodiment of a microcantilever structure. Microcantilever 6 includes deflectable arm 10 and base 16 formed over substrate 18. Substrate 18 may be a conventional semiconductor substrate such as silicon, gallium arsenide, or other suitable materials chosen to be deflectable yet resilient. Microcantilever 6 including deflectable arm 10 is formed using conventional semiconductor processing techniques and the bulk of deflectable arm 10 such as the layers above and below film 14, may preferably be formed of silicon nitride, silicon, or other suitable materials.

Deflectable arm 10 includes top surface 12 and underside 38. It will be seen that overhang portion 34 of deflectable arm 10 will be ultimately positioned over and contacting a sensing element. Deflectable arm 10 includes length 28, height 30 and width 32. The dimensions of microcantilever 6 including deflectable arm 10 will vary according to various embodiments. In an exemplary embodiment, length 28 may range from 100 microns to 200 microns, height 30 may range from 10 microns to 50 microns and width 32 may range from 25 microns to 75 microns but other dimensions may be used alternatively. Furthermore, it should be noted that the essentially horizontal configuration of deflectable arm 10 in its illustrated rest position is exemplary only and that deflectable arm 10 may be formed tilted downward with respect to the horizontal when in its rest position. In that case, the axis of deflectable arm 10 will form an acute angle with each of substrate surface 58 and bottom 56 of substrate 18. It can be seen that one end of deflectable arm 10 is formed integral with substrate 16. In the exemplary embodiment, the end of deflectable arm 10 is fixedly coupled to substrate 18 through base 16 while the opposite end of deflectable arm 10 is free to move in the vertical direction. It should be further noted that, when in rest position, deflectable arm 10 is rigid and fixed into position. Deflectable arm 10 is a resilient member and can be reused after deflecting to detect an analyte. After use as such a detector, resilient deflectable arm 10 returns to its rest position.

Deflectable arm 10 and microcantilever 6 are preferably formed over substrate 18 so as to include overhang portion 34 disposed over substrate 18 upon formation. After the formation of microcantilever 6, substrate 18 is diced or fragmented to produce edge 36 which overhang portion 34 extends beyond. It should be understood that edge 36 of substrate 18 and vertical wall 8 of base 16 are not limited to being coplanar as in the illustrated exemplary embodiment. The critical consideration is that deflectable arm 10 includes overhang portion 34 which extends past edge 36 of substrate 18 so as to enable deflectable arm 10 to be positioned over a sensing element formed on a further surface.

Deflectable arm 10 includes at least one measurable physical property which changes when the arm deflects such as in response to a vertical volumetric expansion of a subjacent contiguous sensing material as will be shown in subsequent figures. An example of a measurable physical property which changes when deflectable arm 10 deflects, is resistance. To provide a resistance which changes when deflectable arm 10 deflects, piezoresisitve member 14 is formed within deflectable arm 10. According to other exemplary embodiments, the piezoresistive member may be formed on top surface 12 or underside 38 of deflectable arm 10.

According to an exemplary embodiment, piezoresistive member 14 may be a film such as barium titanate formed integrally within deflectable arm 10 during the microcantilever fabrication process. When deflectable arm 10 bends, the resistance of piezoresistive member 14 changes due to mechanical stress in the member. The non-stressed resistance of the microcantilevers may be on the order of 2 kohms according to an exemplary embodiment. This exemplary measurable physical property therefore changes due to bending. Detecting means are used to measure this change in resistance. The microcantilevers' sensitivity and the detecting means precision is such that bending of only a few tens of angstroms will result in a measurable resistance change. According to an exemplary embodiment, conductive wires 20 and 24 may be coupled to piezoresistive member 14 through contacts 22 and 26 respectively. Each of contacts 22 and 26 extend through top surface 12 to contact piezoresistive member 14. Conductive wires 20 and 24 represent 2 electrodes coupled to a conventional electric circuit capable of measuring the resistance of piezoresistive member 14.

It should be understood that the measurable physical property of piezoresistivity is intended to be exemplary only. According to other exemplary embodiments, various other physical properties which change when deflectable arm 10 bends may also be used in conjunction with associated detecting means capable of measuring this change. According to a preferred embodiment, the detecting means is capable of measuring the extent of deflection. An electric circuit or other means is provided to facilitate measurement of the change in the measurable physical property. By measuring the change, it is meant that the measurable physical property is preferably measured prior to and after bending and the results compared to detect a change such as associated with the presence of analyte sought to be detected. The degree of change in the physical property will preferably correspond to the degree of arm deflection which, in turn, will preferably correspond to the amount or concentration of analyte present. According to another exemplary embodiment, the deflectable arm may include more than one measurable physical property which changes when the arm deflects.

Figure 2:
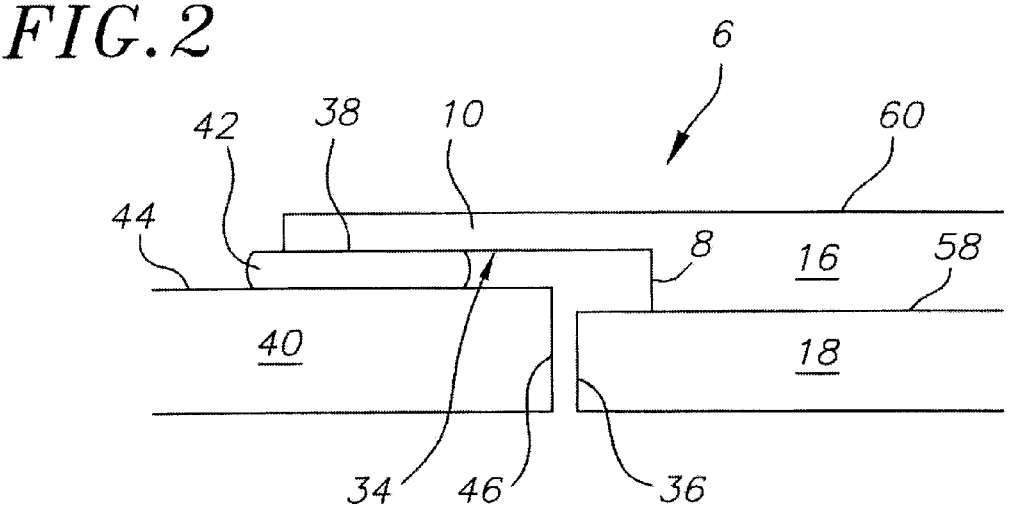
FIG. 2 is a cross-sectional view of an exemplary embodiment of a microcantilever sensor formed over and contacting a sensing element according to the present invention.

FIG. 2 shows an exemplary embodiment of deflectable arm 10 positioned over sensing material 42 formed on surface 44 of further substrate 40. Further substrate 40 may be a ceramic or semiconductor substrate but other materials may be used in other exemplary embodiments. Because overhang portion 34 of deflectable arm 10 extends beyond edge 36 of substrate 18, the components may be positioned such that deflectable arm 10 is disposed superjacent sensing material 42 as shown. Underside 38 of deflectable arm 10 contacts sensing material 42. Edges 46 and 36 are in close proximity so that substrate 18 and further substrate 40 are adjacent one another. Deflectable arm 10 is substantially horizontal and parallel with substrate surface 58. This is intended to be exemplary only and as will be shown in FIGS. 3 and 4, deflectable arm 10 may take on other configurations.

Sensing material 42 may be formed on surface 44 using conventional methods. For the illustrated exemplary embodiment in which sensing element 42 is a discrete pad of material formed on surface 44, sensing material 42 may be formed by drop deposition, such as by using microcapillaries, or using ink jet printer technologies to form a droplet. Other methods for forming discrete sensing element 42 may be used alternatively. Discrete sensing element 42 may take on the shape of a puddle, pad or droplet. Surface 44 may optionally be derivatized prior to formation of the sensing element, to promote adhesion. The dimensions of sensing element 42 are chosen in conjunction with the dimensions of deflectable arm 10. The lateral size of sensing element 42 may be as small as a few microns. The lateral size and length of sensing element 42 along the length of the deflectable arm 10 are chosen to ensure a sufficiently large contiguous portion between sensing element 42 and underside 38 of deflectable arm 10. According to another exemplary embodiment, sensing element 42 may be formed over the entirety of surface 44 of substrate 40. Conventional coating or other methods may be used. Discrete forms of sensing element 42 are preferable when an array of microcantilevers will be used.

Sensing element 42 may be a chemical sensing element or it may be a biological sensing element. For the case of a chemical sensing element, pure polymers or composite materials of combination of polymers can be used to detect either liquid or vapor phase analytes. After formation, polymeric sensing material 42 includes a somewhat rubbery consistency in an exemplary embodiment. The polymeric chemical sensing element is chosen to undergo volumetric expansion or contraction in the presence of at least one analyte sought to be detected. This occurs as the analyte is attracted to and combines with the sensing element, typically by adsorption. Exemplary polymeric chemical sensor materials include poly(vinyl acetate) (PVA), poly(isobutylene) (PIB), poly(ethylene vinyl acetate) (PEVA), poly(4-vinylphenol), poly(styrene-co-allyl alcohol), poly(methylstyrene), poly(N-vinylpyrrolidone), poly(styrene), poly(sulfone), poly(methyl methacrylate), and poly(ethylene oxide). According to another exemplary embodiment, the polymeric chemical sensing material may be a composite material including more than one of the above or other exemplary compounds. Other sensing materials may be used alternatively. Upon exposure to the targeted analyte, the chemical sensor undergoes volumetric expansion including in a vertical direction to deflect deflectable arm 10 in the upward direction when the analyte is adsorbed by the sensing material. According to another exemplary embodiment, when the analyte combines with the sensing element, a volumetric contraction in the vertical direction occurs and the deflectable arm bends downward.

Sensing material 42 may also be a biological sensor such as a biomolecule which undergoes a conformational change in the presence of the analyte sought to be detected. According to one e exemplary embodiment, sensing element 42 may be a thiolated single strand DNA (deoxyribonucleic acid) attached to substrate 40 which may be formed of gold. The thiolated end of the DNA single strand adheres well to gold. Such a biological sensor can be used to detect the complementary DNA strand. DNA preferably exists in a double strand configuration. If the complementary DNA strand (the analyte) is included within the medium introduced to the sensing element, the complementary strand would strongly bind to the thiolated strand effectively increasing the thickness of the DNA layer on the gold substrate or, stated alternatively, produce a volumetric expansion in the vertical direction. According to another exemplary embodiment of a biological sensor, a layer of antibodies, specific to the desired analyte to be sensed such as a particular virus, is formed over surface 40. When the analyte virus is present, it is strongly attracted to and subsequently binds to the antibody layer. In this manner, the layer thickness increases and represents a volumetric expansion in the vertical direction. According to other exemplary embodiments, other biological sensing elements may be used which undergo a physical or morphological change in response to the presence of the analyte sought to be sensed. In each case, the sensing material 42 adsorbs the analyte and expands volumetrically in the vertical direction causing deflectable arm 10 of microcantilever 6 to deflect upward.

According to yet another exemplary embodiment, the biological sensor may be chosen to volumetrically contract in the vertical direction in response to the presence of the analyte sought to be detected.

According to various exemplary embodiments, sensing element 42 may also expand inconsequentially in the lateral direction in addition to in the vertical direction. This depends upon the analyte/sensing material chosen.

Figure 3:
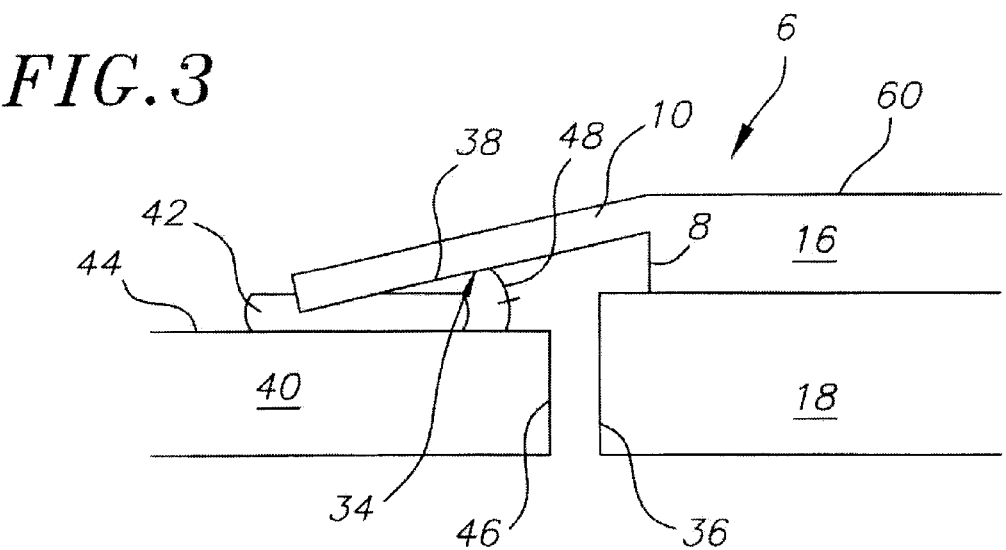
FIG. 3 is a cross-sectional view of an another exemplary embodiment of a microcantilever sensor formed over and contacting a sensing element according to the present invention.
Figure 4:
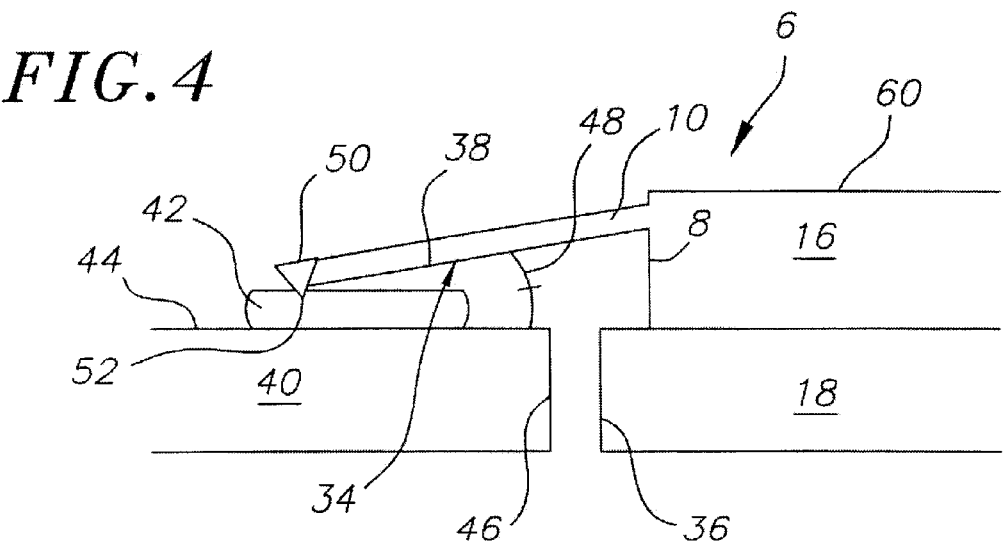
FIG. 4 is a cross-sectional view of yet another exemplary embodiment of a microcantilever sensor formed over and contacting a sensing element according to the present invention.

The various physical configurations of the microcantilever should be pointed out at this point. It can be seen that vertical wall 8 and edge 36 are not coplanar in the exemplary embodiment shown in FIG. 2. FIGS. 3 and 4 show other exemplary embodiments of the microcantilever.

FIG. 3 shows another exemplary embodiment of deflectable arm 10 which is shown in rest position. It can be seen that deflectable arm 10 is angled downward in its rest position. Stated alternatively, the angle 48 which deflectable arm 10 makes with the horizontal in its rest position is an acute angle. Similar to the other exemplary embodiments, deflectable arm 10 includes underside 38 which contacts sensing element 42 when deflectable arm 10 is in its rest position.

FIG. 4 shows another exemplary embodiment in which deflectable arm 10 forms acute angle 48 with the horizontal in its rest position which is illustrated in FIG. 4. In FIG. 4, deflectable arm 10 includes tip 50 which includes contact point 52. Tip 50 is formed as part of the semiconductor fabrication process of deflectable arm 10. Contact point 52 may be a single point or it may be a ledge extending into and out of the plane of the drawing and along the width of deflectable arm 10. Tip 50 including contact point 52 is formed to increase the sensitivity of deflectable arm 10 in response to a volumetric change of sensing material 42 in the vertical direction. Tip 50 may be formed of a different material than the bulk of material used to form deflectable arm 10 or it may be formed of the same material and shaped to include contact point 52 for sensitivity. Top surface 12 of deflectable arm 10 is not coplanar with top surface 60 of base 16 in the exemplary embodiment shown in FIG. 4. It should be understood that in each of the exemplary embodiments shown in FIGS. 1–4, the deflectable arm includes a measurable physical property which changes when the arm bends and which is measurable by detecting means such as an electric circuit coupled to deflectable arm 10.

The materials of construction of deflectable arm 10 are chosen such that deflectable arm 10 bends responsive to a volumetric change of sensing material 42 in the vertical direction, even if deflectable arm 10 is submerged within a liquid medium such as may be introduced to sensing material 42 for analysis.

After an exemplary arrangement such as shown in FIGS. 2–4 is formed, the medium being analyzed for the targeted analyte is introduced to the arrangement such that the medium intimately contacts the sensing material. If the analyte is present in the medium, the sensing material undergoes volumetric expansion in the vertical direction causing upward or downward displacement of the deflectable arm due to deflection of the arm. The degree of displacement will vary with the volumetric change of the sensing material in the vertical direction and also preferably with the concentration or amount of detected analyte. Exemplary deflections of deflectable arm 10 are shown graphically in FIG. 5.

Figure 5:
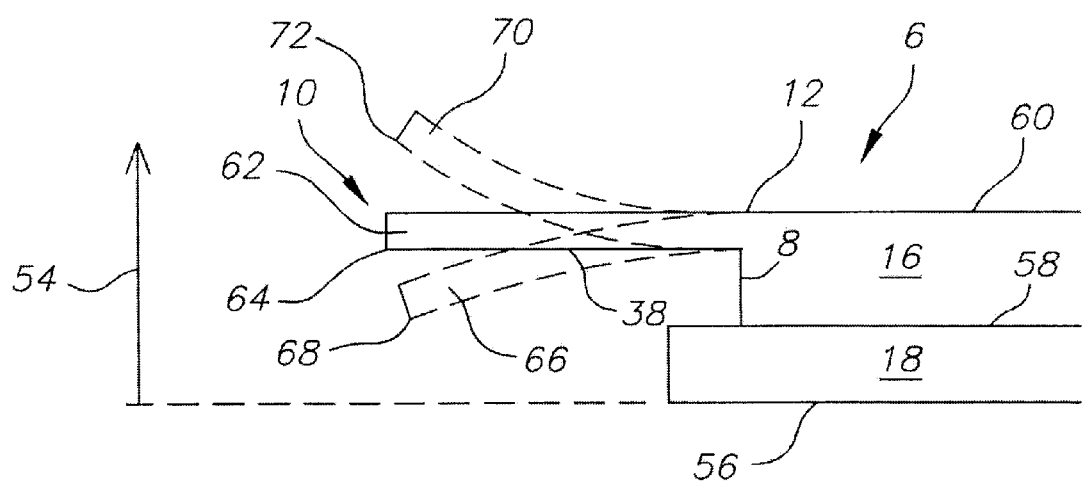
FIG. 5 is a side view of an exemplary microcantilever sensor showing the microcantilever deflected into multiple positions.

Now referring to FIG. 5, deflectable arm 10 of microcantilever 6 is shown to be configured substantially horizontal when in rest position 62. Rest position 62 includes the distal edge of underside 38 disposed at point 64. Exemplary position 70 (shown by dashed lines) shows deflectable arm 10 bent or displaced upward and exemplary position 66 (also shown by dashed lines) shows deflectable arm 10 bent or vertically displaced downward. The amount of vertical displacement along direction 54 may be represented by the vertical displacement between an arbitrary feature of deflectable arm 10, such as the point at the distal end of underside 38 as represented by points 72, 64, and 68 which represent the upper, rest and lower positions, respectively. The extent of vertical displacement or deflection of deflectable arm 10 will be proportional to the amount of volumetric expansion in the vertical direction. According to various exemplary embodiments, the degree of swelling or volumetric expansion in the vertical direction of the sensing element may be proportional to the concentration of the analyte sought to be detected up to a saturation level. According to other exemplary embodiments, this may not be true. Furthermore, according to various exemplary embodiments, the measurable physical property such as resistance of a piezoresistive element may vary linearly with the extent of bending. In other exemplary embodiments this may not be so. Various conventional calibration techniques may be used to correlate the extent of deflection and the associated degree of change of the measurable physical property to the amount or concentration of analyte present.

As above, the sensing material used may be sensitive to a single analyte or to multiple analytes. Furthermore, a composite sensing material may be used to detect any of a number of analytes as indicated by the deflection of the single microcantilever. It is therefore another aspect of the present invention to provide an array of microcantilevers each with an associated sensing element. In this manner, a number of dedicated microcantilevers can be used to detect a particular and distinct analyte. An exemplary array is shown in FIG. 6.

Figure 6:
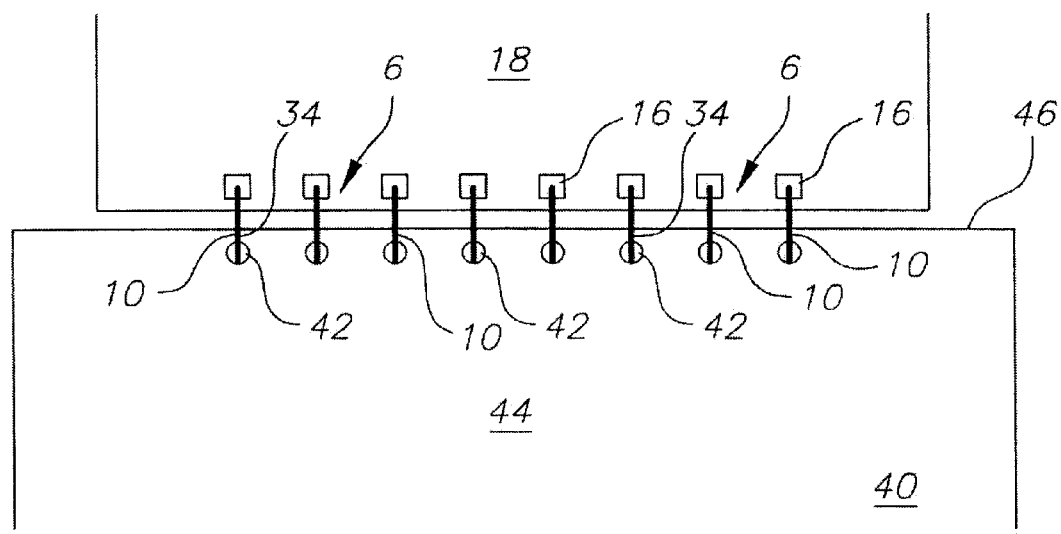
FIG. 6 is a plan view of an exemplary array of microcantilever/sensing materials according to the present invention.

Now referring to FIG. 6, an array of nine microcantilevers is shown. Although a linear array of nine microcantilevers formed on common substrate 18 is shown in the exemplary embodiment of FIG. 6, it should be understood that various numbers of microcantilevers may be included and arranged in different configurations according to various other exemplary embodiments. The microcantilevers are as shown and described in conjunction with previous drawings. Discrete sensing materials 42 are formed on surface 44 of substrate 40. The array of sensing elements 42 is formed to correspond to the complementary array of deflectable arms 10 formed on substrate 18. When substrate 18 and further substrate 40 are positioned in the preferred positions with respect to each other, each deflectable arm 10 is disposed over and in contact with a subjacent discrete sensing element 42. Each microcantilever 6 is also coupled to detecting means such as an electrical circuit (not shown) capable of measuring a change in at least one physical property of deflectable arm 10 when it bends responsive to a volumetric change in the vertical direction of sensing element 42. Each of the discrete sensing elements 42 may be formed of an exemplary chemical or biological sensor such as described above. In the preferred embodiment, each of discrete sensing materials 42 may be formed of a different material. In this manner, each dedicated sensing material 42 is capable of sensing a different analyte and undergoing a volumetric change in response to the presence of such analyte. In this manner, a single medium which may contain multiple analytes sought to be detected may be introduced to the arrangement and the presence and amount (or absence) of the various analytes sought to be detected may be independently determined by a dedicated microcantilever. Principal component analysis of the output of an array of sensors can be used for purposes of analyte identification and quantification. In this manner, a medium may be simultaneously analyzed for the presence of multiple analytes.

As is the case with respect to a single microcantilever, the microcantilever can be calibrated to correlate a measured change in the measurable physical property due to bending, to the amount or concentration of the analyte sought to be detected. In the case where the analyte sought to be detected is not present, the microcantilever does not deflect and therefore the measurements taken before and after the introduction of the medium will be substantially the same.

Accordingly to another exemplary embodiment in which an array of microcantilevers is used, further substrate 40 may be coated with a single coating of a continuous sensing material and multiple microcantilevers may be disposed to contact the sensing material in order to provide multiple readings and a more accurate determination of the analyte or analytes being detected.

It is emphasized at this point that the present invention is not intended to be limited to the exemplary embodiments shown and described above. Rather, the present invention is intended to cover the method and apparatus which the includes the use of a microcantilever having a measurable physical property which changes when the microcantilever bends and which is formed over and in contact with a sensing element which volumetrically changes to deflect the microcantilever in the presence of a particular analyte or analytes sought to be detected.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A microcantilever for detecting at least one analyte in a fluid medium comprising:
   a deflectable arm having one end fixedly coupled to a substrate, said arm being a sensing material on disposed in an initially stationary rest position capable of deflecting responsive to a volumetric change of a subjacent sensing element contacting said arm, and detecting means capable of measuring the deflection of said arm out of said rest position.

2. The microcantilever as in claim 1, wherein said arm includes at least one measurable physical property which changes when said arm deflects and said detecting means is capable of measuring a change in said at least one measurable physical property.

3. The microcantilever as in claim 1, in which said detecting means includes an electric circuit for facilitating measurement of said deflection of said arm.

4. The microcantilever as in claim 1, in which said detecting means includes a transducer capable of transducing said deflection of said arm to a measurable electrical signal.

5. The microcantilever as in claim 1, in which said arm includes a piezoresistive member formed one of therein and thereon and said detecting means includes an electrical circuit capable of measuring a change in resistance of said piezoresistive member due to said deflection.

6. A microcantilever for detecting at least one analyte in a fluid medium comprising:
   a deflectable arm having one end fixedly coupled to a substrate, said arm being disposed in a rest position capable of deflecting responsive to a volumetric change of a subjacent sensing element contacting said arm, and detecting means capable of measuring the deflection of said arm out of said rest position, wherein said arm includes a piezoresistive member formed one of therein and thereon and said detecting means includes an electrical circuit capable of measuring a change in resistance of said piezoresistive member due to said deflection, and wherein said piezoresistive member comprises barium titanate.

7. A microcantilever for detecting at least one analyte in a fluid medium comprising:
   a deflectable arm having one end fixedly coupled to a substrate, said arm being disposed in a rest position capable of deflecting responsive to a volumetric change of a subjacent sensing element contacting said arm, and detecting means capable of measuring the deflection of said arm out of said rest position in which said deflectable arm overhangs an edge of said substrate and said sensing element is disposed on a further substrate.

8. The microcantilever as in claim 1, wherein said sensing element is formed on a surface and said deflectable arm is disposed essentially parallel to said surface when in rest position.

9. The microcantilever as in claim 1, wherein said sensing element comprises a chemical sensor formed of a polymer and which undergoes volumetric expansion in the vertical direction upon exposure to said at least one analyte.

10. The microcantilever as in claim 1, wherein said sensing element comprises a biological sensor formed of layered biological molecules capable of adsorbing said at least one analyte and volumetrically expanding in the vertical direction as a result of said adsorption.

11. The microcantilever as in claim 10, in which said biological sensor comprises antibodies.

12. The microcantilever as in claim 11, in which said at least one analyte comprises a virus attracted to said antibodies.

13. A microcantilever for detecting at least one analyte in a fluid medium comprising:
   a deflectable arm having one end fixedly coupled to a substrate, said arm being disposed in a rest position capable of deflecting responsive to a volumetric change of a subjacent sensing element contacting said arm, and detecting means capable of measuring the deflection of said arm out of said rest position wherein said sensing element comprises a biological sensor formed of layered biological molecules capable of adsorbing said at least one analyte and volumetrically expanding in the vertical direction as a result of said adsorption, and in which said biological sensor comprises a thiolated single strand DNA disposed on a gold substrate.

14. The microcantilever as in claim 13, in which said at least one analyte comprises the complementary DNA strand of double-stranded DNA.

15. The microcantilever as in claim 1, wherein said sensing element comprises at least one of polyvinyl acetate (PVA), polyisobutylene (PIB), polyethylene vinyl acetate (PEVA), poly(4-vinylphenol), poly(styrene-co-allyl alcohol), poly(methylstyrene), poly(N-vinylpyrrolidone), poly(styrene), poly(sulfone), poly(methyl methacrylate), and poly(ethylene oxide).

16. The microcantilever as in claim 1, in which said sensing element comprises a discrete pad of material formed on a surface.

17. The microcantilever as in claim 1, in which said deflectable arm includes silicon nitride as a component thereof.

18. The microcantilever as in claim 1, in which said at least one analyte is included within one of a gaseous medium and a liquid medium.

19. The microcantilever as in claim 1, in which said deflectable arm includes a thickness ranging from 10 microns to 50 microns, a width ranging from 25 microns to 75 microns, and a length ranging from 100 microns to 200 microns.

20. The microcantilever as in claim 1, in which the opposite end of said arm includes a tip having a pointed portion contacting said subjacent sensing element.

21. The microcantilever as in claim 1, in which said detecting means is capable of measuring the extent of said deflection of said arm.

22. An array of microcantilevers for detecting analytes, comprising:
   a plurality of discrete sensing elements formed on a surface;
   a corresponding plurality of deflectable arms each being disposed in a rest position, each having one end fixedly coupled to a substrate and an overhang portion situated superjacent a corresponding sensing element and contacting said corresponding sensing element, each deflectable arm capable of deflecting responsive to a volumetric change in said corresponding sensing element; and
   detecting means capable of measuring the deflection of each deflectable arm out of each said rest position.

23. The array of microcantilevers as in claim 22, wherein each sensing element is different from the other sensing elements.

24. An array of microcantilevers for detecting analytes, comprising:
   a plurality of discrete sensing elements formed on a surface;
   a corresponding plurality of deflectable arms each being disposed in a rest position, each having one end fixedly coupled to a substrate and an overhang portion situated superjacent a corresponding sensing element and contacting said corresponding sensing element, each deflectable arm capable of deflecting responsive to a volumetric change in said corresponding sensing element; and
   detecting means capable of measuring the deflection of each deflectable arm out of each said rest position wherein each sensing element is different from the other sensing elements, and in which said deflectable arms each have one end fixedly coupled to a common substrate and said surface is formed on a further substrate situated adjacent said common substrate.

25. The array of microcantilevers as in claim 22, wherein each sensing element of said plurality of discrete sensing elements undergoes a volumetric change in response to the presence of a different analyte.

26. The array of microcantilevers as in claim 22, in which each deflectable arm includes a piezoresistive element one of therein and thereon and said detecting means includes electrical circuitry for measuring a change in resistance of each piezoresistive element as a result of deflection due to volumetric change in said corresponding sensing element.

27. The array of microcantilevers as in claim 22, in which each said deflectable arm includes at least one measurable physical property which changes when said arm deflects and said detecting means is capable of measuring a change in said at least one measurable physical property of each deflectable arm.

28. The array of microcantilevers as in claim 22, in which each said deflectable arm is dedicated to sensing a distinct analyte.

29. A method for detecting an analyte within a fluid medium, comprising:
   providing a deflectable microcantilever arm having one end fixedly coupled to a substrate, said microcantilever arm disposed in a rest position;
   forming a sensing element subjacent said arm and contacting an underside of said arm, said sensing element capable of at least one of vertical swelling and vertical contraction responsive to the presence of said analyte, said vertical swelling causing said microcantilever arm upward deflection and said vertical contraction causing said microcantilever arm downward deflection;
   introducing a fluid medium containing said analyte to said sensing element, said medium being one of a liquid and a vapor; and
   measuring said deflection of said microcantilever arm out of said rest position.

30. A method for detecting an analyte within a fluid medium, comprising:
   providing a deflectable microcantilever arm having one end fixedly coupled to a substrate, said microcantilever arm disposed in a rest position;
   forming a sensing element subjacent said arm and contacting an underside of said arm, said sensing element capable of at least one of vertical swelling and vertical contraction responsive to the presence of said analyte, said vertical swelling causing said microcantilever arm upward deflection and said vertical contraction causing said microcantilever arm downward deflection;
   introducing a fluid medium containing said analyte to said sensing element, said medium being one of a liquid and a vapor; and
   measuring said deflection of said microcantilever arm out of said rest position wherein said microcantilever arm includes at least one measurable physical property which changes when said microcantilever arm deflects and said measuring comprises measuring a change in said at least one measurable physical property.

31. The method as in claim 29, wherein said microcantilever arm includes a piezoresistive member one of therein and thereon, and said measuring comprises measuring a resistance change of said piezoresistive member as a result of one of said upward deflection and said downward deflection.

32. The method as in claim 31, in which said microcantilever arm includes two conductive leads coupled to said piezoresistive member and said measuring includes measuring resistance across said two conductive leads.

33. The method as in claim 31, in which said measuring includes measuring resistance of said piezoresistive member each of before and after said step of introducing.

34. The method as in claim 31, in which said step of forming said sensing element subjacent said arm includes forming said sensing element on a further substrate and positioning said further substrate adjacent said substrate.

* * * * *

UNITED STATES PATENT AND TRADEMARK OFFICE
CERTIFICATE OF CORRECTION

PATENT NO. : 6,523,392 B2
DATED : February 25, 2003
INVENTOR(S) : Porter et al.

It is certified that error appears in the above-identified patent and that said Letters Patent is hereby corrected as shown below:

Title page,
Item [56], References Cited, U.S. PATENT DOCUMENTS, 5,719,321 A * 2/1998 "Thjundat et al." should be -- Thundat et al. --

Column 9,
Lines 59-61, should read:
-- substrate, said arm being disposed in an initially stationary rest position capable of deflecting responsive to a volumetric change of a sensing material on a --

Signed and Sealed this

Twenty-ninth Day of June, 2004

JON W. DUDAS
*Acting Director of the United States Patent and Trademark Office*